US00PP26638P3

(12) United States Plant Patent
Chapman

(10) Patent No.: US PP26,638 P3
(45) Date of Patent: Apr. 19, 2016

(54) ***CYNODON DACTYLON* L.×*CYNODON TRANSVAALENSIS* L. PLANT NAMED 'C-7'**

(50) Latin Name: ***Cynodon dactylon* L.×*Cynodon transvaalensis* L.**
Varietal Denomination: C-7

(71) Applicant: Sod Solutions, Inc., Mount Pleasant, SC (US)

(72) Inventor: John Chapman, Foley, AL (US)

(73) Assignee: Sod Solutions, Inc., Mount Pleasant, SC (US)

( * ) Notice: Subject to any disclaimer, the term of this patent is extended or adjusted under 35 U.S.C. 154(b) by 122 days.

(21) Appl. No.: 14/120,304

(22) Filed: May 14, 2014

(65) Prior Publication Data

US 2014/0352015 P1 Nov. 27, 2014

Related U.S. Application Data

(60) Provisional application No. 61/855,427, filed on May 15, 2013.

(51) Int. Cl.
*A01H 5/00* (2006.01)

(52) U.S. Cl.
USPC ..... Plt./389

(58) Field of Classification Search
USPC ..... Plt./389
See application file for complete search history.

*Primary Examiner* — Annette Para
(74) *Attorney, Agent, or Firm* — Myers Bigel & Sibley, P.A.

(57) ABSTRACT

A new and distinct variety of Ultra-dwarf Bermuda grass named 'C-7' having a distinctive and unique combination of several characteristics such as: narrow and long leaf blade, deep and long root system, fine texture and dense canopy, uniform light green color, little requirements for maintenance, little inflorescence production and improved cold hardiness.

7 Drawing Sheets

Latin name of the genus and species: The Latin name of the genus and species of the novel variety disclosed herein is *Cynodon dactylon* L.×*Cynodon transvaalensis* L. and therefore characterizes a cross between two species of *Cynodon*, also known as Bermudagrass.

Variety denomination: The inventive variety of *Cynodon dactylon* L.×*Cynodon transvaalensis* L. disclosed herein has been given the variety denomination 'C-7'.

BACKGROUND OF THE INVENTION

The present invention relates to a new and distinct perennial variety of *Cynodon dactylon* L.×*Cynodon transvaalensis* L.

'C-7' (also referred to herein as Sunday) is a 2007 selection from a Bermuda "green" at Cotton Creek Golf Course in Southern Alabama. The parent grasses are unknown. During the mid-80's, John Chapman, a Craft Farms employee, made several selections from an undefined green at Cotton Creek Golf Course known in the area as "Cotton Creek Dwarf". One of the selections produced a genetically stable line with superior characteristics and was named 'C-1'. Samples of 'C-1' were isolated and expanded in a protected environment. In April of 1987 Cotton Creek Golf Course sprigged its greens with 'C-1' and those greens have remained stable and performing well since then. 'C-7', hereafter known as Sunday, is a 2007 selection from 'C-1' greens at Cotton Creek Golf Course. 'C-7' has been protected from commercial use until genetically stability could be confirmed. 'C-7' has been genetically stable since its selection in 2007. Fine leaf texture and improved cold hardiness are two reasons that make 'C-7' a unique and different type of Ultra-dwarf Bermudagrass. Other characteristics that make 'C-7' unique are its dense canopy, lighter green color and reduced production of seedheads. It is anticipated that the plant of this invention will be marketed under the synonym Sunday as a trade name. 'C-7' is so identified in pictures and morphological and agronomic charts of this disclosure.

SUMMARY OF THE INVENTION

'C-7' is a distinctive variety of *Cynodon dactylon* L.×*Cynodon transvaalensis* L. having a lighter green (10GY 6/4 on a Munsell Color Chart), a longer and deeper root system, fine leaf texture with denser canopy, little inflorescence production and excellent cold hardiness. 'C-7' is a very poor seed producer, making it suitable for vegetative reproduction only, such as sprigs, rhizomes, plantlets, or sod. 'C-7' is adapted for use in the hot-humid, and transition zone areas in the US, zones 6a to 11 of the Plant Heat Zone Map.

DESCRIPTION OF THE NEW VARIETY

The following is a detailed description of the new grass variety, based upon observations of the plant grown in pots at a research area located near Starkville, Miss. 'C-7' is an outstanding Ultra-dwarf Bermudagrass cultivar with fine texture, long leaf blade and uniform color. Its fine texture produces a dense canopy and its long leaves result in less scalping, both ideal conditions for putting green surfaces in golf courses. 'C-7' also exhibits longer internode lengths and reduced production of inflorescences/seed-head which are desirable characteristics for golf greens. 'C-7' has an improved cold hardiness exhibiting little winter damage and winter-kill after the winter, making it suitable for use in the transition zone. 'C-7' has a deep, long and strong root system, which helps the variety to extract water and nutrients from deeper profiles. 'C-7' can only be established vegetatively by sprigs, rhizomes, plugs or sod. 'C-7's uniform green color (10 GY 6/4 on a Munsell Color Chart) and fine texture, combined with reduced maintenance needs, make it a highly appealing turfgrass for golf greens.

Dimensions of Morphological Structures

Figure 1:
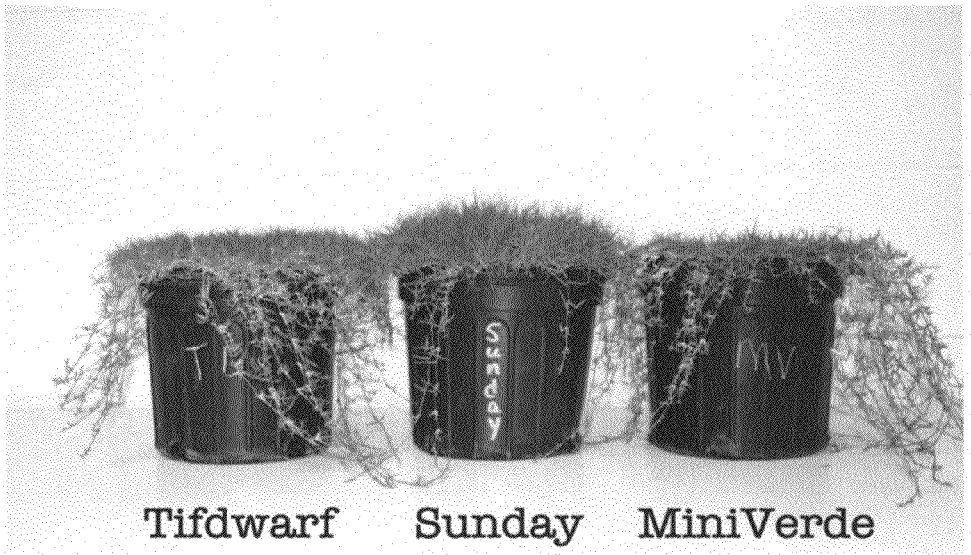
FIG. 1: 'C-7' (Sunday) and others planted in pots at a research facility; Starkville, Miss.
Figure 2:
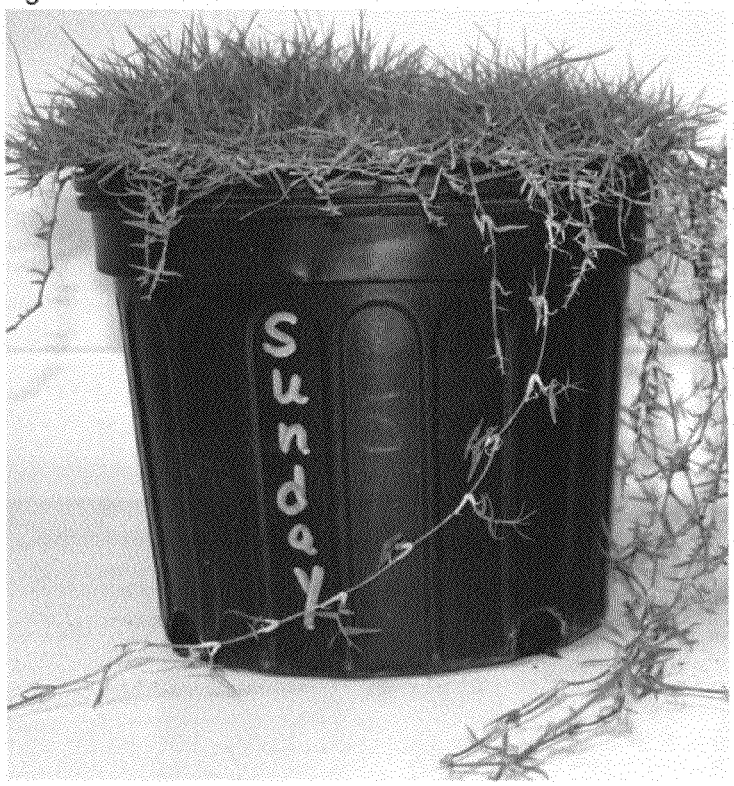
FIG. 2: 'C-7' (Sunday) pot for evaluation inside a greenhouse near Starkville, Miss.

'C-7' was compared to 2 cultivars of Ultra-dwarf Bermuda grasses and one experimental line in a study planted near Starkville, Miss. starting in January 2012. Each variety was planted in 1 gallon pots; four-inch diameter plugs were thinly sliced to remove roots and washed free of soil (FIG. 1 and FIG. 2). One plug was placed on each pot. There were 5 pots of each cultivar. Pots used potting mix: Redi-earth Plug and Seedling Mix (Sungro Horticulture, Bellevue, Wash.) and were kept at a green-house to produce plant material for morphological evaluations. Plant material was collected using a completely random experiment design with 4 replications (pots). Greenhouse complex had natural sunlight conditions. The pots were allowed to grow for 4 weeks, and then were clipped on Feb. 23, 27 and Mar. 1, 2012 to encourage density and stolon development. They were allowed to grow un-mowed for another 4 weeks before measurement. The leaf blade measurements were conducted in April and May 2012. Fifty randomly selected leaf blades from each cultivar were measured for length and width. Width was measured at the widest point of the blade. Fifty randomly internode measurements were collected in April and May, 2012 from stolons that grew off each pot.

The Analysis of Variance (ANOVA) indicated that cultivars differed significantly for most variables measured (Table 1).

TABLE 1

Analysis of Variance for Ultra-dwarf Bermuda grass cultivars comparisons with 'C-7' conducted during 2012.

| | Mean Squares of the traits | | |
|---|---|---|---|
| Source | ID (mm) | IL (mm) | LL (mm) |
| Variety | 0.449** | 597.57** | 3683.8** |
| Error | 0.009 | 22.03 | 43.84 |
| CV | 11.73 | 20.03 | 25.08 |

| | Mean Squares of the traits | | |
|---|---|---|---|
| Source | LW (mm) | PH (mm) | W/L |
| Variety | 0.410** | 11.25** | 0.023** |
| Error | 0.033 | 0.094 | 0.0003 |
| CV | 13.77 | 7.80 | 30.67 |

ID—Internode Diameter,
IL—Internode Length,
LL—Leaf Length (mm),
LW—Leaf Width (mm),
PH—Plant Height,
W/L—Leaf width/length ratio
**Significant at 1% level Cultivars showed significant differences on all analyzed morphological characteristics (Table 1). Internode Diameter (ID), Internode Length (IL), Leaf Length (LL), Leaf Width (LW), Plant Height (PH) and Leaf Width/Length Ratio (L/W) were significantly different at 1% level (Table 1). The evaluations were well conducted and produced reliable results as demonstrated by the low Coefficients of Variation (CV) (Table 1).

Inflorescences were never observed on 'C-7' during 18 months of evaluation period, which is a strong indication 'C-7' has very little inflorescence production.

'C-7' had the longest leaf blade length (37.9 mm) when compared to 'Tifdwarf', 'MiniVerde' and the other experimental line used as comparisons (Table 2). Visual differences on leaf length and width can be seen in FIG. 3. 'Tifdwarf' and 'MiniVerde' have significantly shorter leaf blades compared to 'C-7'. Leaf blade lengths for 'Tifdwarf' and 'MiniVerde' were 20.68, and 19.07 mm, respectively; while 'C-7' leaf blade length was 37.0 mm, nearly double (Table 2). 'C-7' also had the narrower leaf blade width (1.25 mm) among the tested varieties (Table 2). 'Tifdwarf' was the commercial variety with the closest leaf blade width (1.36 mm) to 'C-7' but still significantly different than 'C-7' (Table 2). The leaf blade width difference between the two varieties was 0.11 mm; which is greater than 0.07 mm, the least significant difference (LSD) at 5% level (Table 2). 'MiniVerde' leaf width (1.44 mm) was much wider than 'C-7' falling on a third different statistical category (Table 2) and indicating 'C-7' has a unique narrow leaf blade.

TABLE 2

Ultra-dwarf Bermuda cultivars comparisons with 'C-7' conducted during 2012.

| | Internode | | Leaf Blade | |
|---|---|---|---|---|
| Cultivar | Diameter (mm) | Length (mm) | Width (mm) | Length (mm) |
| 'C-7' | 0.77 b | 24.87 a | 1.25 c | 37.90 a |
| 'MSB-264' | 0.86 a | 23.60 b | 1.26 c | 27.94 b |

TABLE 2-continued

Ultra-dwarf Bermuda cultivars comparisons with 'C-7' conducted during 2012.

| Cultivar | Internode Diameter (mm) | Internode Length (mm) | Leaf Blade Width (mm) | Leaf Blade Length (mm) |
|---|---|---|---|---|
| Tifdwarf | 0.77 b | 24.76 a | 1.36 b | 20.68 c |
| MiniVerde | 0.75 b | 20.74 c | 1.44 a | 19.07 c |
| LSD (0.05) | 0.02 | 1.00 | 0.07 | 2.60 |

LSD (0.05) = Least significant difference at 5% level. Means followed by the same letter are not different at 5%.

Figure 4:
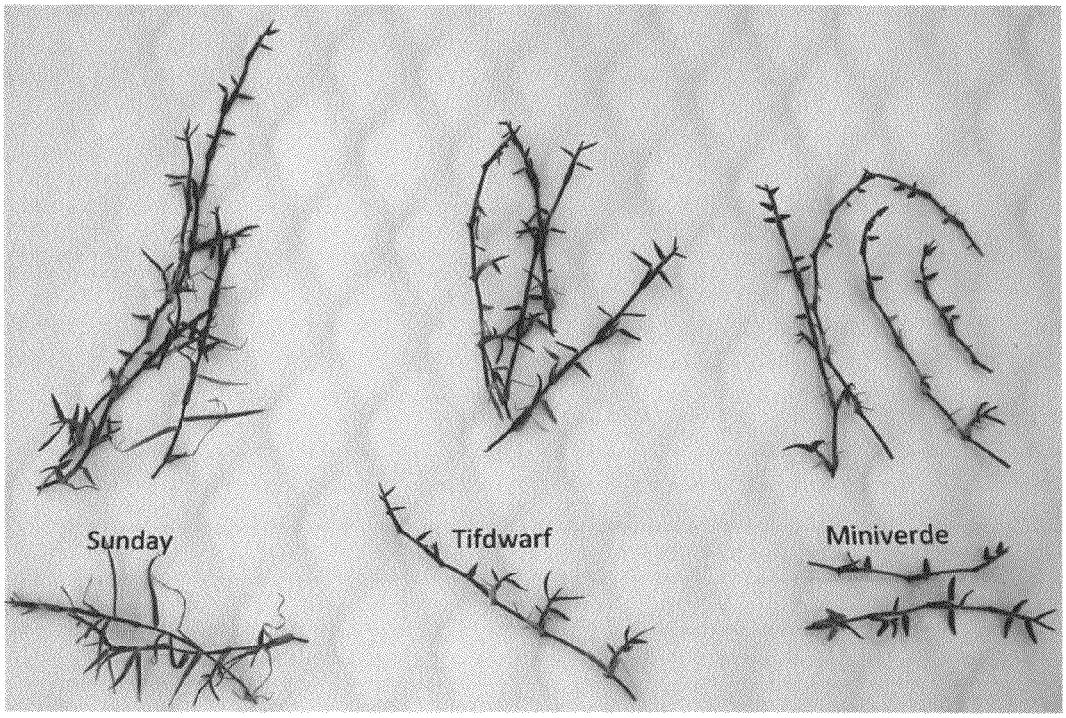
FIG. 4: Sprig and stolon details of 'C-7 (Sunday)', 'Tifdwarf' and 'MiniVerde'.

'C-7' and 'Tifdwarf' have similar stolons at naked eye, while 'MiniVerde's stolons exhibit a more distinct pattern (FIG. 4). Internode diameters were very similar between 'C-7', 'Tifdwarf' and 'MiniVerde', with no statistical differences (Table 2). 'MSB-264' fell in a different category with internode diameters of 0.86 mm statistically wider than 'C-7' (Table 2). Table 2 shows 'C-7' with the longest internode length (24.87 mm), being statistically different than 'MiniVerde' (20.74 mm) and 'MSB-264' (23.60 mm), but not statistically different than 'Tifdwarf' (24.76 mm).

Finer texture is an expression of leaves with fine blade width. Because 'C-7' has such narrow leaf blade, it produces a dense canopy which is ideal for golf practices, making the golf ball stand and roll perfectly in the golf green. The long leaf blade, longer than the other varieties tested (Table 2), allows for 'C-7' to produce less scalping than most of Bermudagrass varieties for greens. Less scalping is an important and desired trait, making possible for golf managers and superintendents to reduce cost with less mowing. The relation: leaf width/length can be used to identify a long and narrow leaf. Long and narrow leaves are represented by low values. The leaf width/length for 'C-7' (0.035) was the lowest among the tested varieties (Table 3), being statistically different than all other entries (Table 3). It indicates 'C-7' was the variety with the longest narrower leaves tested.

Figure 5:
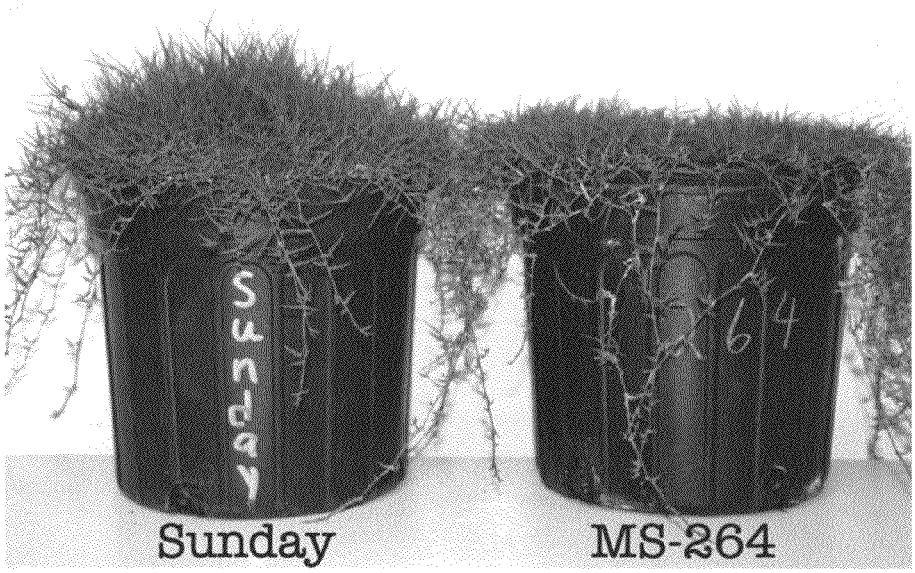
FIG. 5: Plant heights for 'C-7' (Sunday) and 'MSB-264'.
Figure 6:
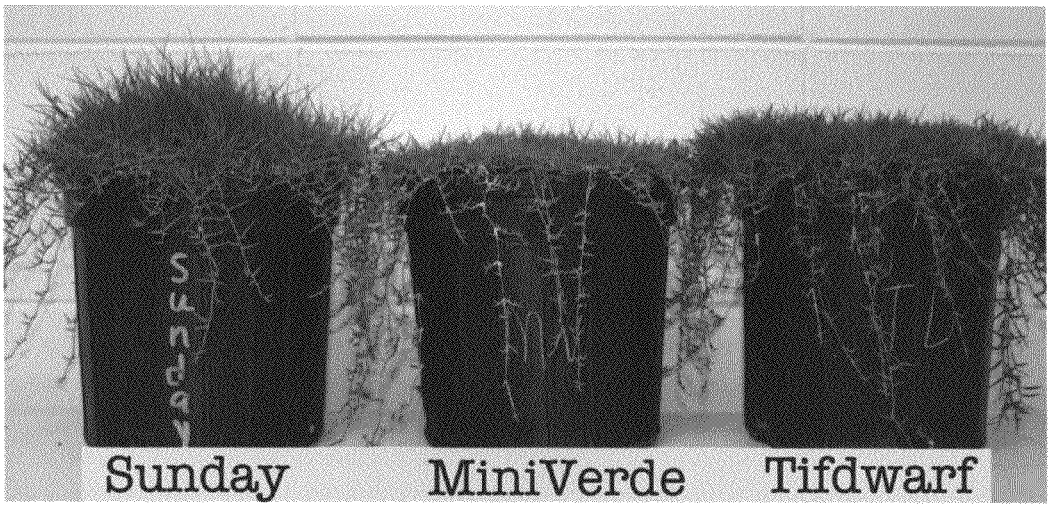
FIG. 6: Plant heights for 'C-7' (Sunday), 'Tifdwarf' and 'MiniVerde'.

Another distinct characteristic for 'C-7' is its plant height. Table 3 shows plant heights for all tested varieties. 'C-7' had the lowest value (6.1 cm) which was statistically different than 'MSB-264' (3.4 cm), Tifdwarf (3.5 cm) and MiniVerde (2.7 cm) (Table 3). Visual assessment and differences for plant heights are shown in FIGS. 5 and 6.

Figure 3:
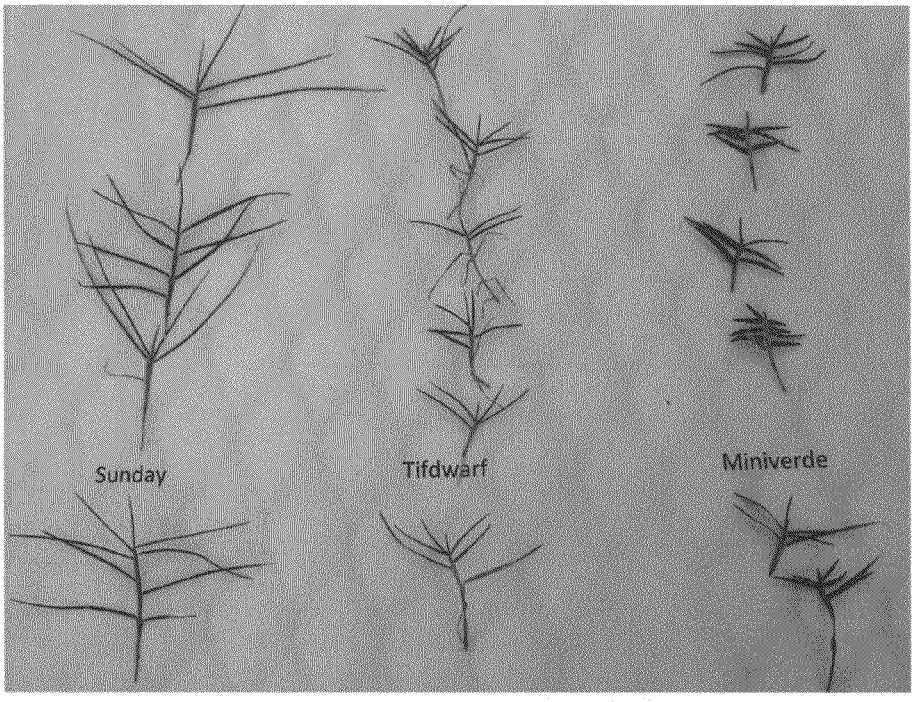
FIG. 3: Leaf details of 'C-7' (Sunday), 'Tifdwarf' and 'MiniVerde'.

Internode measurements are shown on Table 2, with 'C-7' exhibiting the longest internode length (24.9 mm) compared to 'Tifdwarf' (24.8 mm), 'MSB-264' (23.6 mm) and 'MiniVerde' (20.7 mm). Internode length for 'C-7' was statistically different than 'MiniVerde' and 'MSB-264', but it was not from 'Tifdwarf' (Table 2). Internode diameter averages were similar and not statistically different between 'C-7' (0.77 mm), 'Tifdwarf' (0.77 mm) and 'MiniVerde' (0.75 mm) (Table 2). The only variety with a statistically different average was 'MSB-264' (0.86 mm). Sprigs and stolons of 'C-7', 'Tifdwarf' and 'MiniVerde' are shown in FIG. 3.

TABLE 3

Plant height and Leaf blade width/length ratio. April and May 2012

| Cultivar | Leaf length - LL (mm) | Leaf width - LW (mm) | Ratio LW/LL | Plant height - PH (cm) |
|---|---|---|---|---|
| 'C-7' | 37.90 a | 1.25 c | 0.035 a | 6.10 a |
| 'MSB-264' | 27.94 b | 1.26 c | 0.048 c | 3.40 b |
| 'Tifdwarf' | 20.68 c | 1.36 b | 0.069 b | 3.50 b |

TABLE 3-continued

Plant height and Leaf blade width/length ratio. April and May 2012

| Cultivar | Leaf length - LL (mm) | Leaf width - LW (mm) | Ratio LW/LL | Plant height - PH (cm) |
|---|---|---|---|---|
| 'MiniVerde' | 19.07 c | 1.44 a | 0.082 a | 2.70 d |
| LSD (0.05) | 2.60 | 0.07 | 0.007 | 0.4 |

LSD (0.05) = Least significant difference at 5% level. Means followed by the same letter are not different at 5%.

Root System

A root study was established in a green-house facility near Starkville, Miss. Plugs of 'C-7', 'Champion', 'Tifdwarf', and 'MiniVerde' were planted on Aug. 13, 2013 in lysimeters 4 inches in diameter and 16 inches in depth. The bottom 4 inches was filled with gravel and the top 12 inches with 100% sand. A 100% sand growing media was used to ensure roots were completely free of debris prior to root analysis. Each plug of sod was washed free of soil and roots uniformly trimmed below the thatch layer prior to transplanting into the lysimeters. A starter fertilizer was applied to each lysimeter at 1 lb/1000 $ft^2$ prior to transplanting. Liquid urea was then applied to lysimeters weekly at a rate of 0.2 lbs/1000 $ft^2$. Once established, cultivars were mowed daily at 0.125 inches using a handheld 7.2 volt cordless sheer with clipping removal and watered daily (if needed) to prevent wilt. Destructive root samplings were initiated around 90 days after planting, by Nov. 14, 2013.

Data collection includes root biomass, root length density (RLD), and specific root length (SRL). A root measuring software, WinRhizo, provides a computerized method for analyzing scanned root images to quantify RLD and SRL, which provides detailed information regarding root morphology. Specifically, SRL is the ratio of root length to root dry weight and indicates the amount of root length per gram of dry weight. Essentially, the WinRhizo takes each individual root and connects them all together to make one long root, therefore, providing a far more accurate method of determining root length than simply taking a root core and measuring the longest root with a ruler. A high SRL value indicates a thin, long and highly branched root system. A thin, high volume and long root system, has the ability to better uptake water and nutrients, stabilize soil, store energy more efficiently, and increase stress tolerance. Meanwhile, RLD measures the total root length per volume of soil.

TABLE 4

Root biomass, root length density and specific root length of four Ultra-dwarf Bermudagrass cultivars. November 2013.

| Cultivar | Root Biomass (g) | Root Length Density - RLD (m/cm3) | Specific Root Length (SRL) (cm) |
|---|---|---|---|
| 'C-7' | 0.56 a | 1.89 a | 5,954 a |
| 'TifEagle' | 0.31 b | 1.42 ab | 5,260 ab |
| 'Champion' | 0.30 b | 1.22 ab | 3,982 be |
| 'MiniVerde' | 0.27 b | 0.78 c | 3,519 c |
| LSD (0.05) | 0.158 | 0.511 | 1,633.5 |

LSD (0.05) = Least significant difference at 5% level. Means followed by the same letter are not different at 5%.

Cultivars showed significant differences on root biomass, root length density (RLD) and specific root length (SRL) (Table 4).

Figure 7:
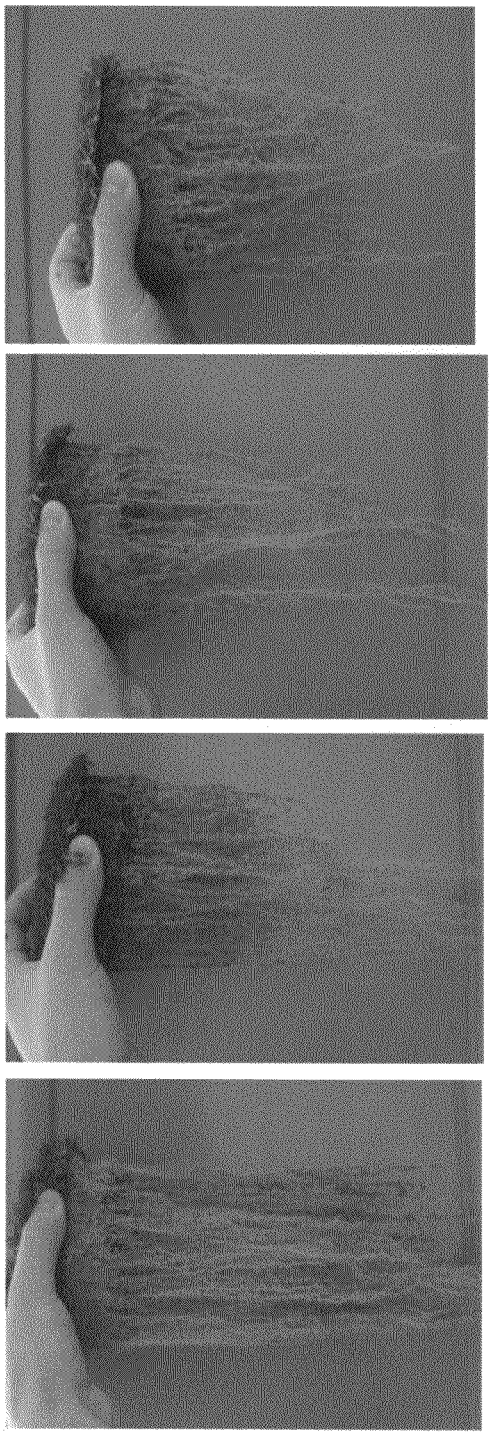
FIG. 7: Root System of 'C-7' (Sunday) (first panel), Champion (second panel), Mini-Verde (third panel) and Tifdwarf (fourth panel), MS. 2013.

'C-7' had the highest root biomass (0.56 g) amongst all tested varieties (Table 4). The variety with the second highest root biomass was 'TifEagle' (0.31 g), which was almost half of the root biomass for 'C-7' (Table 4). All varieties were grouped in the same statistical category (b), while 'C-7' was the only one to stand in a different statistical category (a) (Table 4). That strongly indicates 'C-7' has a bigger and stronger root system compared to the other entries. 'C-7' bigger root biomass can be easily visualized in FIG. 7, which shows all tested varieties right before being measured, after 90 days of growing conditions.

'C-7' exhibited the highest root length density (1.89 m/cm3) amongst all tested varieties (Table 4). 'C-7' root length density value was higher but not statistically different than 'TifEagle' (1.42 m/cm3), but it was significantly different (higher) than 'Champion' (1.22 m/cm3), and 'Mini-Verde' (0.78 m/cm3) (Table 7).

'C-7' also had the highest specific root length (5,954 cm), compared to 'TifEagle' (5,260 cm), 'Champion' (3,982 cm) and 'Mini-Verde' (3,519 cm) (Table 4). The specific root length of 'C-7' was significantly different than 'Champion' and 'Mini-Verde' (Table 4), clearly indicating that 'C-7' has a longer root system, compared to other ultra-dwarf Bermudagrass' varieties tested. Fast putting greens require the superintendent to lower mowing heights, which is often detrimental to Bermudagrass putting green root systems. 'C-7' has a long and strong root system with high root biomass per volume of soil, allowing it to compensate the stress of very low mowing heights displaying good visual quality and excellent playability.

Growth Habits

Lateral Growth

A comparison study was installed in 3 locations: a sod farms, near Arcadia, Fla.; a sod farm near Rembert, S.C. and a golf course near Beaufort, S.C. All locations were installed in July 2011 to evaluate the speed of lateral growth of 'C-7' and other varieties of Ultra-dwarf Bermudagrasses. All entries were planted using plugs produced in 72 cell trays. Plugs were planted in 10×30 ft. plots, using 12 inch centers. Plots were fertilized with 10 lbs. of 10-05-05/1000 sq. ft. spread immediately after planting the plugs, and watered in. Irrigation was applied at least once a week, until plugs were fully grown in. Entries were: 'C-7', 'MSB-264', 'Tifdwarf' and 'MiniVerde'. Evaluations of percentage of ground covered (%) by the varieties and visual quality ratings (1 to 9, with 9=highest quality) were collected from July to October of 2011 (Tables 5 and 6).

Figure 8:
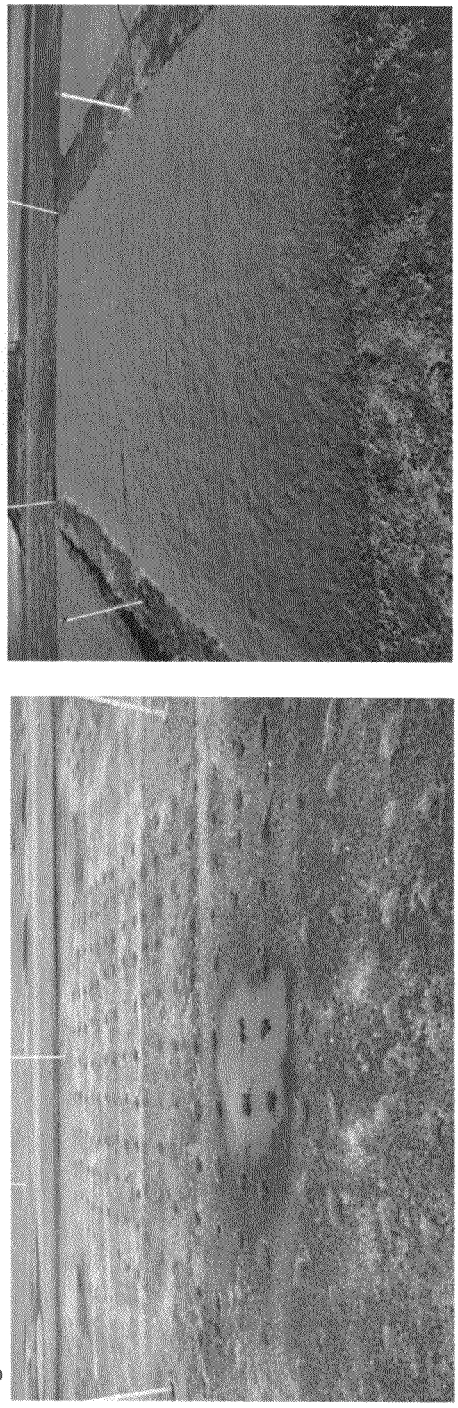
FIG. 8: Test plots with 'C-7' and other entries near Arcadia, Fla. 2011.

The first variety to reach an average of 100% of ground cover (Table 5) was 'MSB-264' followed closely by 'C-7' (FIG. 8), It is important to notice that 'C-7' grew in faster than the 'Tifdwarf' and 'MiniVerde', indicating it can establish quicker than those commercial varieties of ultra-dwarfs (Table 5). Normally, a variety that grows in fast also repairs itself fast.

TABLE 5

Ground cover of 'C-7' and other entries - 2011. Average of 3 locations.

| | Ground cover (%) | | | | | |
|---|---|---|---|---|---|---|
| Varieties | 7/21 | 8/4 | 8/25 | 9/15 | 10/05 | 10/27 |
| 'C-7' | 5 | 25 | 40 | 85 | 97 | 100 |
| 'MSB-264' | 5 | 30 | 45 | 95 | 100 | 100 |
| 'Tifdwarf' | 5 | 20 | 30 | 80 | 90 | 97 |
| 'MiniVerde' | 5 | 25 | 40 | 85 | 95 | 100 |

Figure 9:
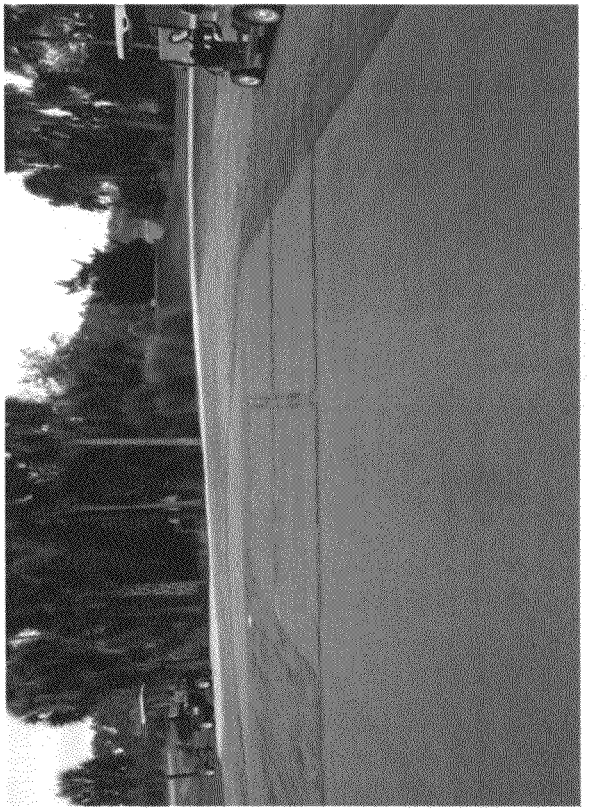
FIG. 9: 'C-7' test plots near Rembert, S.C. and Beaufort, S.C. 2011.
Figure 9:
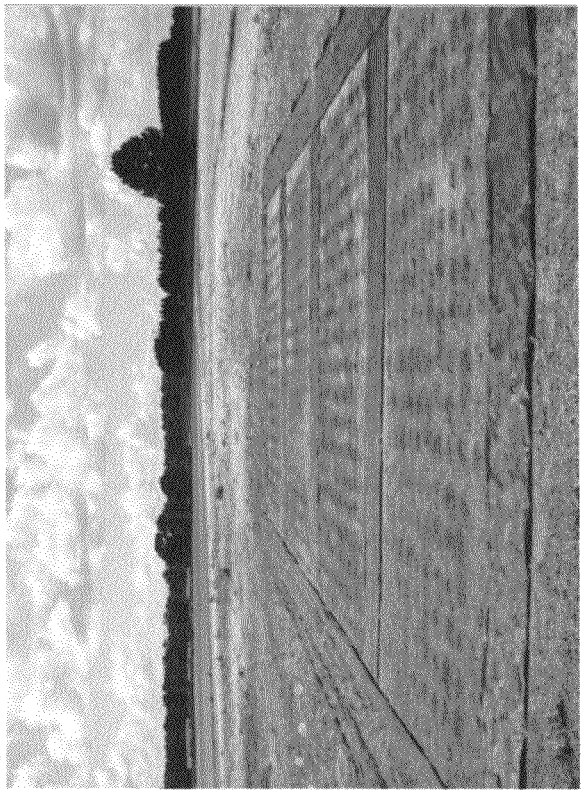
Figure 10:
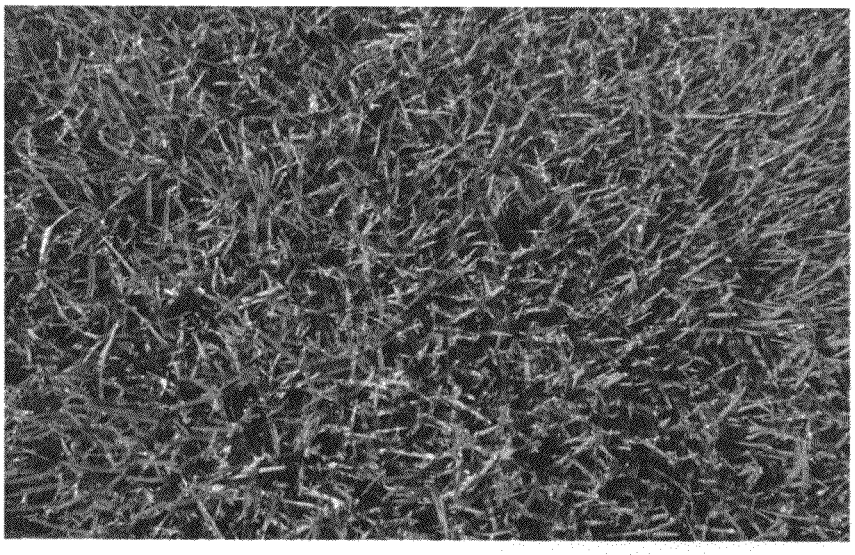
FIG. 10: Close-up detail of 'C-7' test plot planted near Arcadia, Fla. 2011.

Repairing itself quickly is an important and desirable characteristic for an ultra-dwarf variety, since it can significantly reduce the maintenance cost with fertilizers and topdress sand. The same plots planted near Arcadia, Fla., Rembert, S.C. and Beaufort, S.C. were used to evaluate visual quality (FIG. 9). Visual quality ratings took in consideration the following aspects: color, density, uniformity and texture. 'C-7' exhibited the best average visual quality ratings (8.00) recorded along the tested period (Table 6). The uniform light green color of 'C-7' (10 GY 6/4 on a Munsell Color Chart), combined with its fine texture and density (Table 2); result in an aesthetically beautiful and homogeneous playing surface for golf greens (FIG. 10).

TABLE 6

Quality Ratings of 'C-7' and other entries - 2011. Average of 3 locations.

| | Quality Visual Ratings (1-9) | | | | | | |
|---|---|---|---|---|---|---|---|
| Varieties | 7/21 | 8/4 | 8/25 | 9/15 | 10/05 | 10/27 | Average |
| 'C-7' | 7 | 8 | 8 | 8 | 8 | 9 | 8.00 |
| 'MSB-264' | 7 | 7 | 8 | 8 | 8 | 8 | 7.67 |
| 'Tifdwarf' | 7 | 7 | 6 | 6 | 6 | 6 | 6.33 |
| 'MiniVerde' | 7 | 7 | 7 | 7 | 7 | 8 | 7.17 |

9 = Best possible rate

Cold Tolerance

Figure 11:
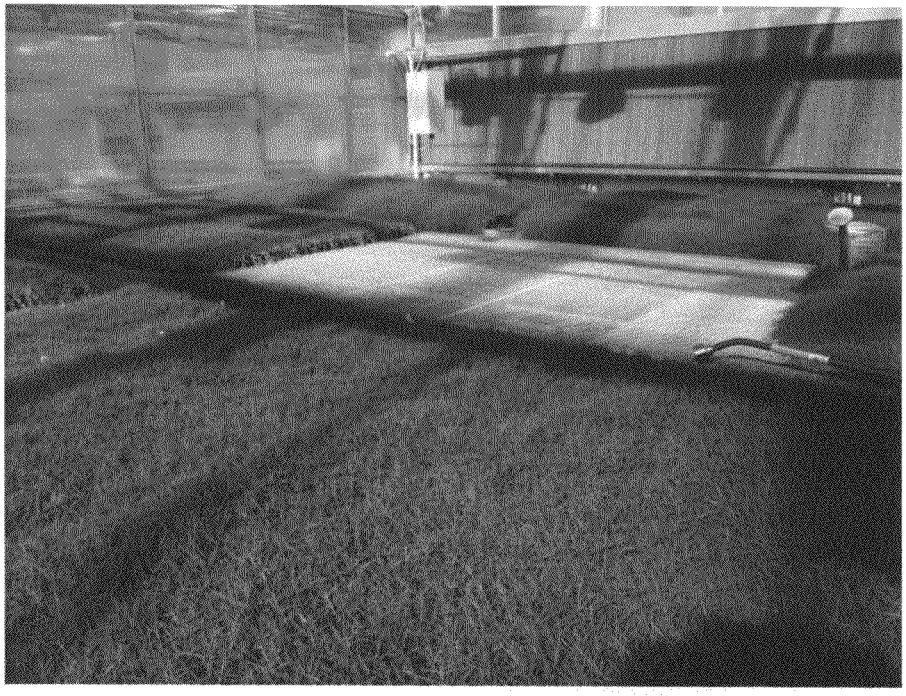
FIG. 11: 'C-7' sprigs being reproduced in a green-house near Stillwater, Okla. 2012.
Figure 12:
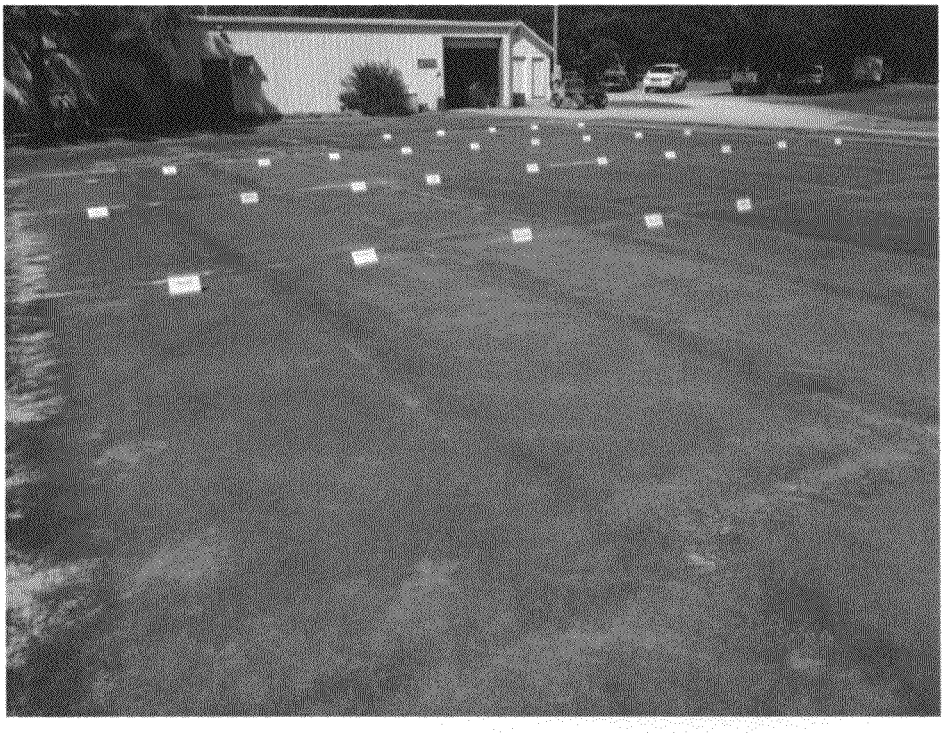
FIG. 12: Cold tolerance evaluation test area near Stillwater, Okla. 2012.

'C-7' was planted as part of an experiment designed to evaluate and compare the cold tolerance of several experimental lines to traditional commercial varieties of ultra-dwarf Bermuda types. All entries will be evaluated for the amount of winter damage they can sustain when used in the transition zone of the United States (Zone 7 and 6b USDA Plant Hardiness Zone Map). The experiment was planted in a research area near Stillwater, Okla. using 5×5 ft. plots replicated 5 times randomly. Plots were planted by June 2012, with sprigs using a 1:8 planting ratio and standard fertilization regime to grow in. Plots will be maintained at golf greens height =0.125 inches, after establishment period. Sprigs used on the experiment were produced in a green-house (FIG. 11). A total of 15 entries are being tested, ten experimental lines and 5 commercial varieties (FIG. 12). First results of genetic color, late season color retention, frost tolerance, spring green up, monthly quality, percent live coverage, leaf texture and shoot density will be available by summer 2013 and a second year evaluation results by summer 2014.

Preliminary results indicate 'C-7' has a very good cold tolerance, which is consistent with anecdotal information coming from golf courses testing 'C-7' informally in parts of Northern Alabama and Tennessee.

That which is claimed is:

1. A new and distinct variety of Ultra-dwarf Bermuda grass named 'C-7', as herein illustrated and described, is characterized by its distinctive and unique combination of several characteristics such as: narrow and long leaf blade, deep and long root system, fine texture and dense canopy, uniform light green color, little requirements for maintenance, little inflorescence production and improved cold hardiness.

* * * * *